US00PP36847P2

(12) United States Plant Patent
Jones et al.

(10) Patent No.: US PP36,847 P2
(45) Date of Patent: Jul. 22, 2025

(54) ***SORBARIA* PLANT NAMED 'Hyfaria'**

(50) Latin Name: *Sorbaria sorbifolia*
Varietal Denomination: Hyfaria

(71) Applicants: John Jones, Newtown (GB); Maria Jones, Newtown (GB)

(72) Inventors: John Jones, Newtown (GB); Maria Jones, Newtown (GB)

(73) Assignee: HYFRYD PLANTS, Newtown (GB)

( * ) Notice: Subject to any disclaimer, the term of this patent is extended or adjusted under 35 U.S.C. 154(b) by 0 days.

(21) Appl. No.: 19/026,103

(22) Filed: Jan. 16, 2025

Related U.S. Application Data

(60) Provisional application No. 63/555,340, filed on Feb. 19, 2024.

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Sorbaria sorbifolia* plant named 'Hyfaria' that is characterized by its compact plant habit, its large leaves, its young foliage that is intensely deep red in color with the red color holding into summer.

3 Drawing Sheets

Botanical classification: *Sorbaria sorbifolia.*
Variety denomination: 'Hyfaria'.

CROSS REFERENCE TO RELATED APPLICATIONS

This application claims priority to a U.S. Provisional Patent Application, Application No. 63/555,340 filed Feb. 19, 2024 under 35 U.S.C. 119(e), the entire contents of which is incorporated by reference herein. This application is also related to a European plant breeders' rights application filed on Mar. 26, 2024, application Ser. No. 20/240,737. The Applicant received the information for the Plant breeders' rights application directly from the Inventor.

BACKGROUND OF THE INVENTION

The present invention relates to a new and distinct cultivar of *Sorbaria sorbifolia* and will be referred to hereafter by its cultivar name, 'Hyfaria'. 'Hyfaria' is a new cultivar of false spirea, a shrub grown for use as a landscape plant.

The new *Sorbaria* arose from a breeding program conducted by the Inventors at a nursery in Newtown, Powys, The United Kingdom. The objective of the breeding program was to develop a new *Sorbaria* cultivar with bright red young foliage.

The new *Sorbaria* originated by open pollination in July of 2012 of *Sorbaria sorbifolia* 'Sem' (U.S. Plant Pat. No. 16,336) as the female parent. The male parent is therefore unknown. 'Hyfaria' was selected as a single unique plant from the resulting seedlings in 2014.

Asexual propagation of the new cultivar was first accomplished by the Inventor using stem cuttings in June of 2015 in Newtown, Powys, United Kingdom. Asexual propagation by stem cuttings has determined that the characteristics of 'Hyfaria' are stable and reproduced true to type in successive generations.

SUMMARY OF THE INVENTION

The following traits have been repeatedly observed and represent the characteristics of the new cultivar. These attributes in combination distinguish 'Hyfaria' as a unique cultivar of *Sorbaria.*

1. 'Hyfaria' exhibits a compact plant habit.
2. 'Hyfaria' exhibits large leaves.
3. 'Hyfaria' exhibits young foliage that is intensely deep red in color with the red color holding into summer.

The female parent plant of 'Hyfaria' is similar to 'Hyfaria' in having young foliage that is red in color, mature foliage that is green in color, and a similar leaf shape. The female parent plant of 'Hyfaria' differs from 'Hyfaria' in having young foliage that is lighter red in color and changes to a green color earlier in the season, and leaves that are smaller in size. 'Hyfaria' can also be compared to the *Sorbaria sorbifolia* cultivar 'Bococot' (U.S. Plant Pat. No. 33,639). 'Bococot' is similar to 'Hyfaria' in having young foliage that is red in color, mature foliage that is green in color, and a similar leaf shape. 'Bococot' differs from 'Hyfaria' in having young foliage that changes to green earlier in the season, leaves that are smaller in size, and seedpods that are red in color.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include website listings by Hortweek, Genesis Plant Marketing, Plantipp and Peter Plantipp, franciscusvandewiel (instagram), Wyevale Nurseries, RHS, Cowell's Garden Center, Coolings Garden Centre, The Bowa Garden Centre, Hort News, Porcupine PR, Horticulture Week, Stewarts Garden Centre, Darby Nursery Stock, Floral Daily, Seiont Nurseries, Rare Plants Ireland, Christina Walker, and Florapedia.

BRIEF DESCRIPTION OF THE DRAWINGS

The accompanying color photographs illustrate the overall appearance and distinct characteristics of the new *Sorbaria*. The photographs were taken of a 2-year-old plant of 'Hyfaria' as grown in a 27-cm circular container in a conventional unheated greenhouse in Boskoop, The Netherlands.

The photograph in FIG. 1 illustrates the overall appearance of the plant habit of 'Hyfaria'.

Figure 1:
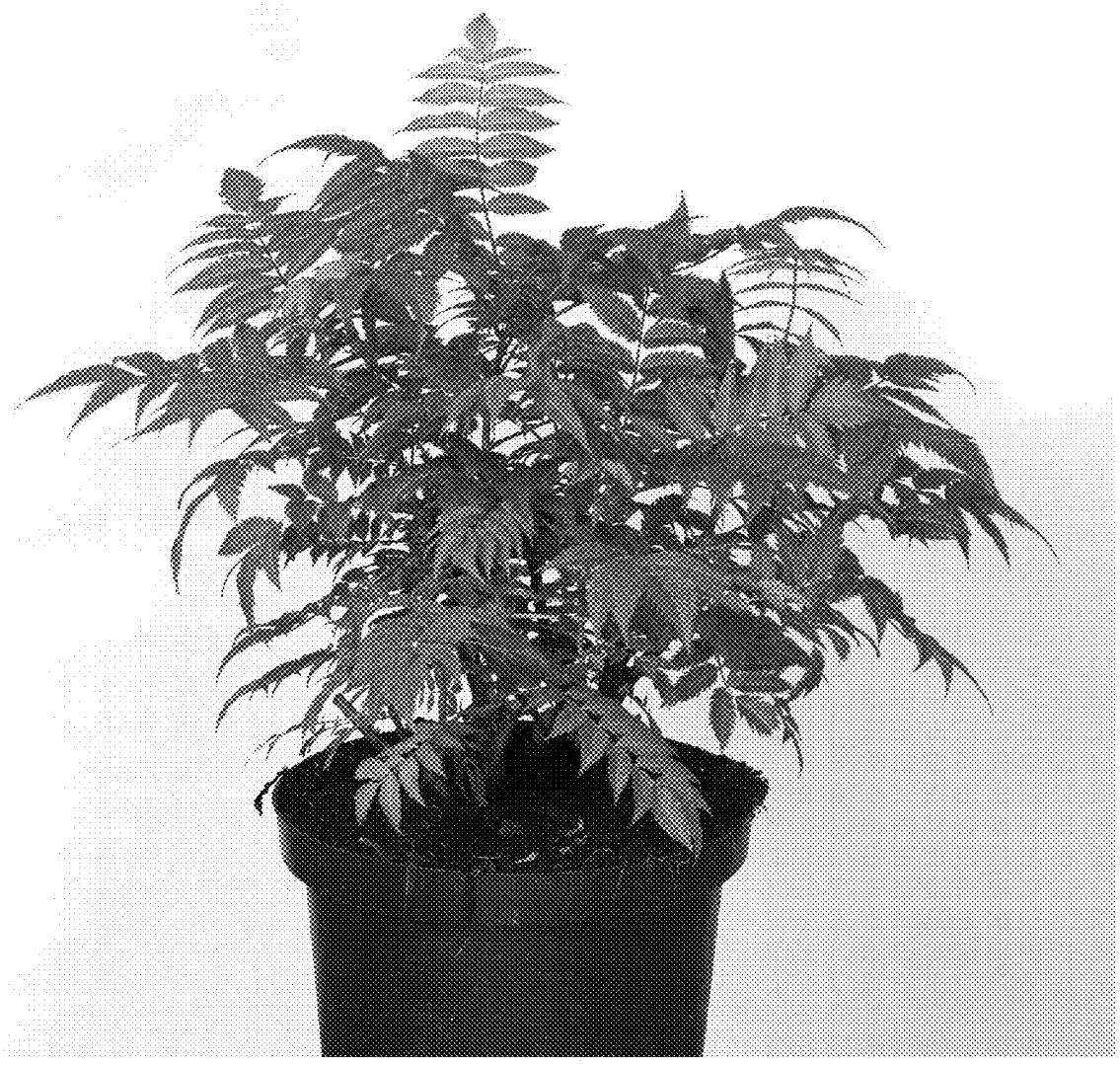
Figure 2:
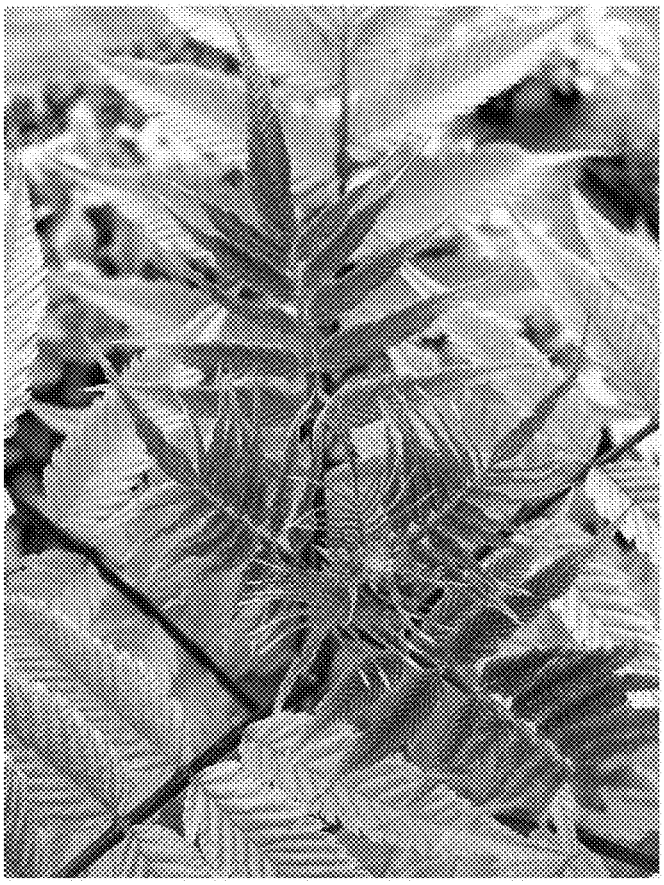

The photograph in FIG. 2 provides a close-up view of the young foliage of 'Hyfaria'.

Figure 3:
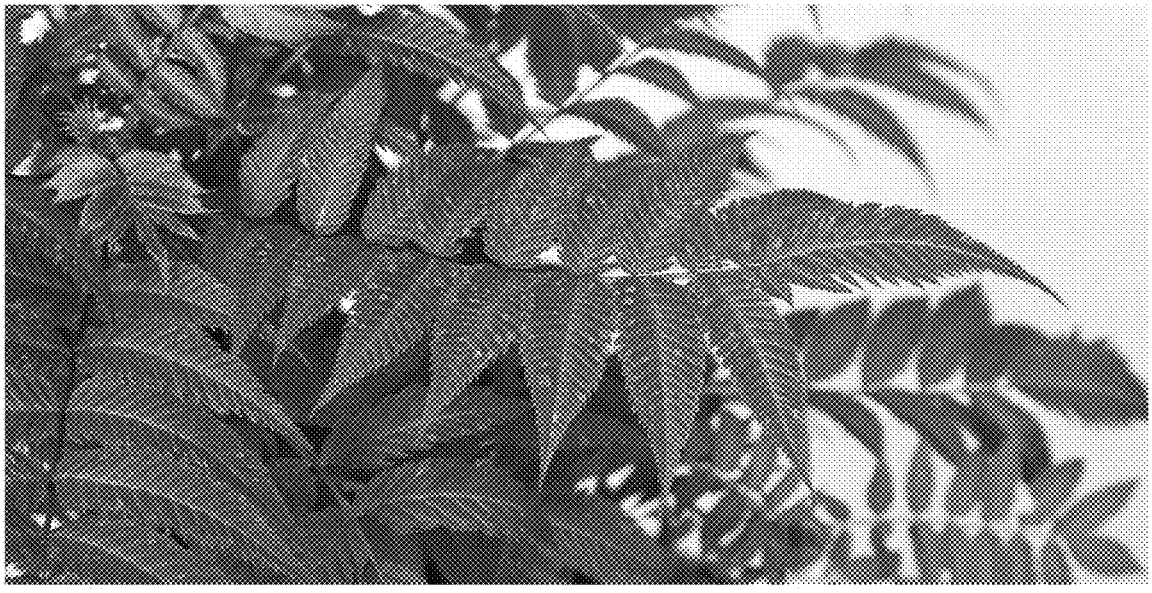

The photograph in FIG. 3 provides a close-up view of the mature foliage of 'Hyfaria'.

Figure 4:
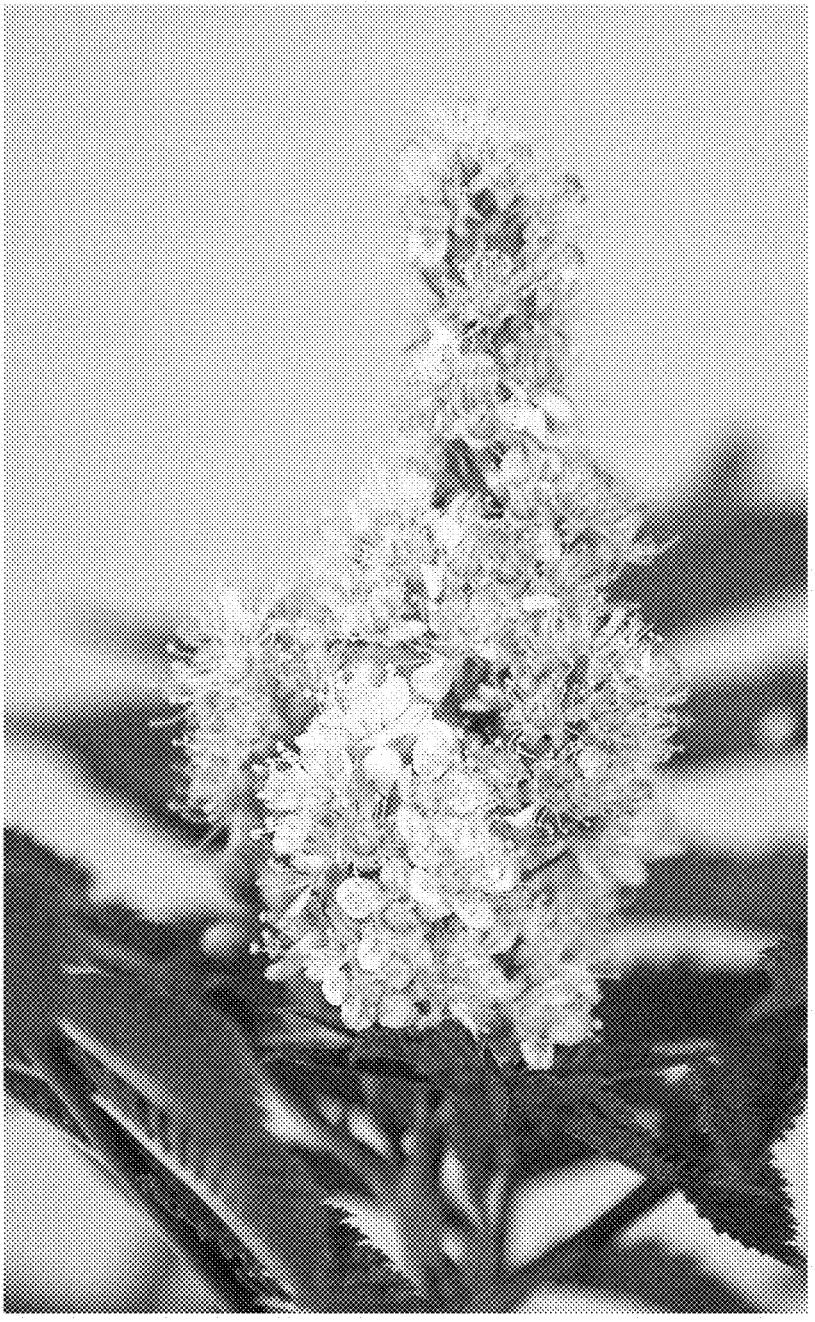

The photograph in FIG. 4 provides a close-up view of an inflorescence of 'Hyfaria'.

The colors in the photographs are as close as possible with the digital photography techniques utilized and the color values cited in the detailed botanical description accurately describe the colors of the new *Sorbaria*.

DETAILED BOTANICAL DESCRIPTION

The following is a detailed description of 2-year-old plants of the new *Sorbaria* as grown in 27-cm containers in a conventional unheated greenhouse in Boskoop, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—July to August in The Netherlands.

*Plant type*.—Deciduous shrub, perennial.

*Plant habit*.—Compact, upright and broadly spreading.

*Height and spread*.—Average of 45 cm in height and 60 cm spread as a 2-year-old plant grown in a container.

*Hardiness*.—At least in U.S.D.A. Zones 3 to 9.

*Diseases and pests*.—No resistance or susceptibility to diseases or pests has been observed.

*Root description*.—Fibrous, slightly to moderately outward spreading by underground rhizomes.

*Propagation*.—Stem cuttings.

*Root development*.—An average of 3 weeks for root initiation and a young rooted plant is produced in about 12 weeks from a rooted cutting.

*Growth rate*.—Moderate.

Stem description:

*Stem strength*.—Strong.

*Stem shape*.—Rounded.

*Stem size*.—Average of 12.4 cm in length and 4 mm in width.

*Stem surface*.—Young and mature stems are matte and glabrous.

*Stem color*.—Young; 143C, mature; 144A, older bark; 199B and N199A.

*Stem aspect*.—Average of 40° from main branch (varying between 30° and 50°).

*Internode length*.—Average of 1.8 cm.

*Stem quantity*.—Average of 8 main branches and 12 lateral branches.

Foliage description:

*Leaf shape*.—Broad oblong to slightly obovate.

*Leaf division*.—Compound.

*Leaf aspect*.—Slightly carinate.

*Leaf arrangement*.—Alternate.

*Leaf*.—Petiolate.

*Leaflet quantity*.—Average of 7 leaflets per leaf.

*Leaflet shape*.—Narrow ovate to nearly lanceolate.

*Leaflet base*.—Acute to broadly acute.

*Leaflet apex*.—Long and narrowly apiculate.

*Leaflet fragrance*.—None.

*Leaflet venation*.—Pinnate, veins furrowed, upper surface; 144A to 144B, lower surface 145A.

*Leaflet margins*.—Biserrate, very slightly undulate, unlobed.

*Leaflet surface*.—Both surfaces smooth, glabrous, nonrugose, upper surface matte to very slightly glossy, lower surface very slightly glossy.

*Leaf/leaflet size*.—Whole leaf; average of 22.4 cm in length and 13 cm in width, terminal leaflet; average of 8.1 cm in length and 3.2 cm in width. lateral leaflets; average of 7.1 cm in length and 2.2 cm in width.

*Leaflet color*.—Young upper surface; 180A, changing to 174B and 174C, then changing to 152D before maturing, young lower surface; 179A, changing to 173B and 173C, then changing to 152D before maturing, mature upper surface; 137B, mature lower surface; a color between 146A and 147B.

*Petioles*.—Average of 3.9 cm in length (from base to base of top of lowest leaflet) and 3 mm in diameter, flattened, both sides smooth and glabrous and very slightly glossy, strong, color; upper surface 144A, slightly to strongly tinged 166A, lower surface 144B.

*Rachis*.—Average of 14.5 cm in length (from base to base of top of top leaflet) and 3 mm in diameter, flattened, both sides smooth and glabrous and very slightly glossy, strong, color; upper surface 144A, slightly to strongly tinged 166A, lower surface 144B.

*Stipules*.—2 leafy stipules at the base of each leaf, narrow elliptic in shape, average of 1 cm in length and 3 mm in width, narrow apiculate apex, narrow cuneate base, both surfaces glabrous and slightly glossy, color; young both surfaces 144B, mature both surfaces 143A and 143B.

Inflorescence description:

*Inflorescence type*.—Terminal panicle.

*Inflorescence size*.—Average of 4.6 cm in diameter and 8.9 cm in height.

*Flower quantity*.—Average of 225 per inflorescence, 900 flowers and buds per plant.

*Lastingness of inflorescence*.—Individual flowers average of one week, self-cleaning.

*Flower type*.—Single.

*Flower aspect*.—Rotate, upright to slightly outward.

*Flower fragrance*.—Moderate, unpleasant.

*Flower buds*.—Broadly ovate in shape, average of 4 mm in length and 2.5 mm in diameter, color; NN155D, immature sepals 144D, apex tinged 177B.

*Flower size*.—Average of 6 mm in depth, 8 mm in diameter.

*Peduncle*.—Average of 8.1 cm in length, 1.75 mm in diameter, held in a vertical angle, strong, smooth, matte and glabrous surface, color; 143C, sunny side tinged 183A.

*Pedicels*.—Average of 3 mm in length, 1 mm in diameter, held in an average angle of 45°, strong, smooth, matte and glabrous surface, color; 144C.

*Calyx*.—Rotate, average of 2 mm in length, 4 mm in diameter.

*Sepals*.—Rotate, 5, 1 whorl, 1.5 mm in length, 1.2 mm in width, apex acute, broadly ovate and reflexed in shape, entire margins; both surfaces matte, smooth, glabrous, when opening and fully upper surface 147D, when opening and fully open lower surface 144D, apex 177B.

*Petals*.—Rotate, 5 per flower, 1 whorl, unfused, 3 mm in length, 2.5 mm in width, ovate, moderately concave in shape, rounded tip, cuneate base, entire margins, smooth, glabrous, slightly velvety, non-rugose, matte, color; upper and lower surface when opening 155C, upper and lower surface when fully open NN155D.

Reproductive organs:

*Gynoecium*.—Pistil; 5, average of 2.5 mm in length, style; 2.2 cm in length, 157B, stigma; 3 mm in length and diameter, club-shaped, 158D in color, ovary; 145D in color.

*Androecium*.—Stamens; 22 (varying between 20 and 25), filaments; NN155D in color, average of 3 mm in length, anthers; dorsifixed, double broadly ovate in shape, 0.5 mm in length, 0.4 mm in width, 155A, pollen; low in quantity, 156D in color.

*Fruit and seed*.—None observed.

It is claimed:

1. A new and distinct cultivar of *Sorbaria* plant named 'Hyfaria' as herein illustrated and described.

* * * * *